United States Patent [19]

Mericle

[11] Patent Number: 4,991,764
[45] Date of Patent: Feb. 12, 1991

[54] SURGICAL STAPLING INSTRUMENT

[75] Inventor: Robert Mericle, Raleigh, N.C.

[73] Assignee: Edward Weck Incorporated, Princeton, N.J.

[21] Appl. No.: 300,523

[22] Filed: Jan. 23, 1989

[51] Int. Cl.$^5$ .............................................. A61B 17/00
[52] U.S. Cl. ...................................... 227/178; 227/19; 227/180
[58] Field of Search ................ 227/19, 175, 176, 177, 227/178, 179, 180

[56] References Cited

U.S. PATENT DOCUMENTS

| | | |
|---|---|---|
| D. 272,851 | 2/1984 | Green et al. |
| D. 272,852 | 2/1984 | Green et al. |
| 3,078,465 | 2/1963 | Bobrov .................................. 227/19 |
| 3,079,606 | 3/1963 | Bobrov et al. ........................ 227/19 |
| 3,317,105 | 5/1967 | Astafjev et al. ...................... 227/19 |
| 3,490,675 | 1/1970 | Green et al. ......................... 227/19 |
| 3,499,591 | 3/1970 | Green .................................. 227/19 |
| 3,973,709 | 8/1976 | Akopov et al. ...................... 227/19 |
| 4,111,206 | 9/1978 | Vishnevsky et al. ................ 227/19 |
| 4,216,890 | 8/1980 | Akopov et al. ...................... 227/19 |
| 4,241,861 | 12/1980 | Fleischer ............................. 227/19 |
| 4,244,372 | 1/1981 | Kapitanov et al. .................. 227/19 |
| 4,290,542 | 9/1981 | Fedotov et al. ..................... 227/19 |
| 4,328,805 | 5/1982 | Akopov et al. ...................... 227/19 |
| 4,397,311 | 8/1983 | Kanshin et al. ..................... 227/19 |
| 4,402,444 | 9/1983 | Green .................................. 227/19 |
| 4,429,695 | 2/1984 | Green .................................. 227/19 |
| 4,520,817 | 6/1985 | Green .................................. 227/19 |
| 4,596,351 | 6/1986 | Fedotov et al. ..................... 227/19 |
| 4,605,001 | 8/1986 | Rothfuss ............................. 227/19 |
| 4,608,981 | 9/1986 | Rothfuss et al. ................... 227/19 |
| 4,610,383 | 9/1986 | Rothfuss et al. ................... 227/19 |
| 4,633,861 | 1/1987 | Chow et al. ........................ 227/19 |
| 4,633,874 | 1/1987 | Chow et al. ........................ 227/19 |

Primary Examiner—Paul A. Bell
Attorney, Agent, or Firm—Robert E. Lee; Gene Warzecha

[57] ABSTRACT

A surgical stapling instrument includes first and second body members pivotally and detachably connected to each other, each having an elongated jaw to grip tissue therebetween to be stapled together. The instrument further includes a toggle joint pivotally connected on one of said body members and adapted to engage the other body member to lock the body members together. Various latching mechanisms are provided to releasably latch the proximal ends of the body members together prior to locking the jaws about the tissue to be stapled.

15 Claims, 3 Drawing Sheets

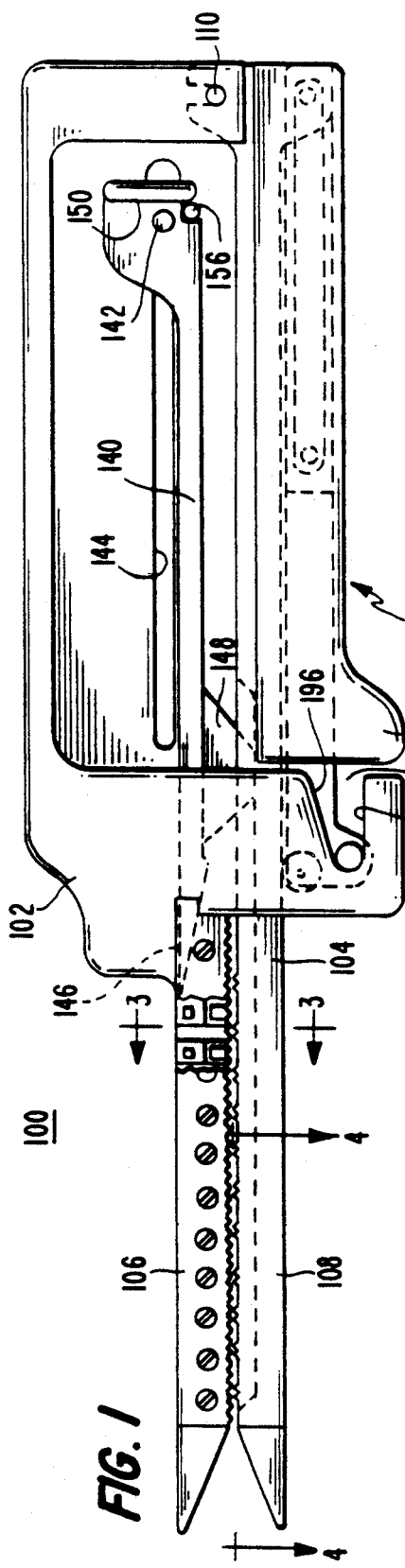
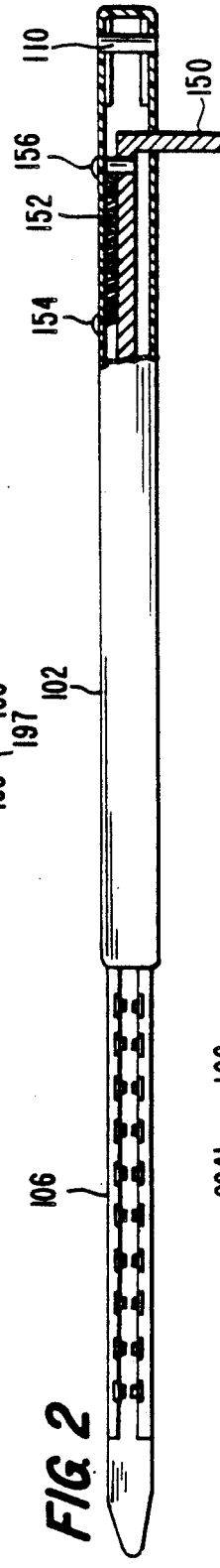
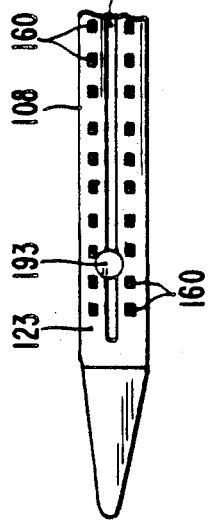
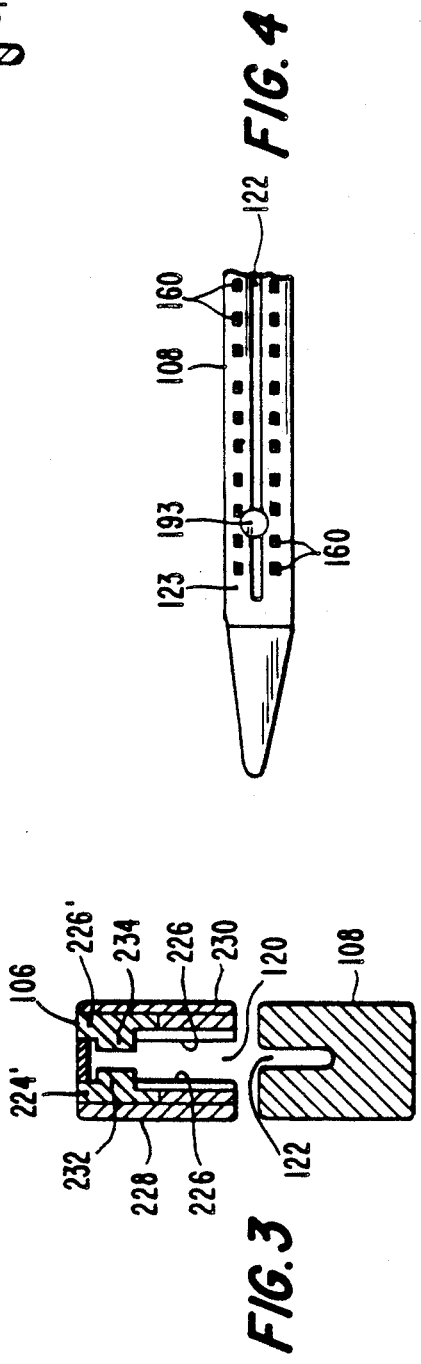
FIG. 1
FIG. 2
FIG. 4
FIG. 3

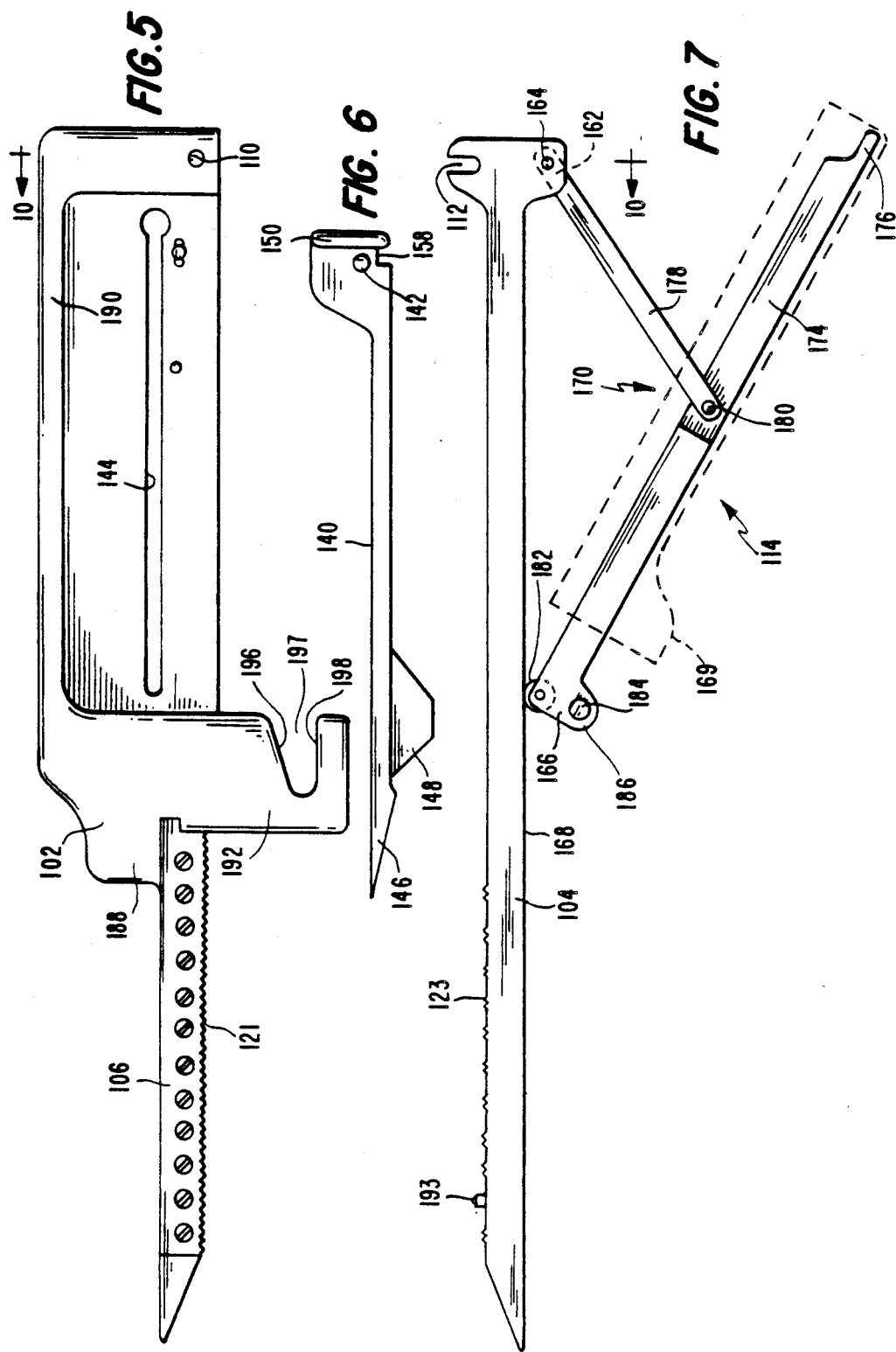

SURGICAL STAPLING INSTRUMENT

BACKGROUND OF THE INVENTION

This invention relates to surgical instruments and more particularly to a surgical instrument for applying spaced rows of staples to internal organs. Instruments of this type include a pair of elongated jaw members, one of which carries a staple cartridge with rows of staples and the other of which carries an anvil. A pusher bar and knife assembly is moved along the jaws to eject the staples by a camming action acting on the staple pushers associated with the individual staples to close the staples against the anvil through the tissue gripped between the jaws. The knife cuts the tissue along a line between the staple rows. One instrument of this type is disclosed, for example, in U.S. Pat. No. 3,079,606.

Forces needed to clamp or compress the tissue between the jaws in instruments such as these must be overcome when locking the jaws together. It also is desirable in certain instances to be able to latch releasably the proximal ends of the body members carrying the jaws before clamping the tissue between the jaws.

SUMMARY OF THE INVENTION

It is an object of the present invention to provide a surgical stapling instrument of the type described above in which the action of locking the instrument to overcome tissue clamping forces is accomplished with greater ease.

It is a further object of the present invention to provide a surgical stapling instrument which can be releasably latched together prior to locking the instrument when clamping the tissue between the jaws.

A surgical stapling instrument capable of internal stapling procedures is provided having first and second body members which are pivotally and detachably connected to each other, each body having an elongated jaw. One of the jaws is adapted to receive longitudinal rows of staples. An elongated bar is provided which is slidable longitudinally along said jaws to eject staples from one jaw and shape the staples against anvil means provided on the other jaw to form rows of staples in tissue gripped between the jaws. Locking means are provided for releasably locking said jaws in a tissue gripping staple inserting position which means include a toggle joint with a first end pivotally mounted to one of said body members, a second end adapted to engage the same body member distally of the first end of the toggle joint. The toggle joint also includes a knee disposed between the first and second ends of the toggle joint. The second end of the toggle joint is also adapted to engage a portion of the other body member to lock the jaws in tissue gripping position when the knee is straightened.

More particularly the toggle joint includes a lever bar which engages the one body member at one end and a linking bar pivotally mounted to the one body member. The linking bar at its other end is pivotally connected to the lever bar intermediate its ends. In one embodiment, a freely rotatable roller is mounted to the lever bar at the end which distally engages the one body member. The roller provides a low friction engagement.

The other body member includes a frame having spaced apart sides which extend away from the other body member and are adapted to receive the one body member therebetween. The spaced apart sides each have a slot aligned with one another and these slots receive a pin mounted in the end of the lever bar which engages the one body as the knee of the toggle joint is straightened.

The frame of the instrument includes a first handle portion while a second handle portion is attached to the lever bar, the handle portions facilitating gripping of the instrument by the user.

A surgical stapling instrument is provided with latching means for releasably latching the proximal ends of the first and second body members. In one embodiment a key hole slot is provided in one body member and a pin movable between first and second positions is coupled to the other body member. The pin is biased in the first position. When the pin is moved to the second position a narrowed portion of the pin will enter the key hole slot. When the pin returns to the second position, the pin is locked in the slot. A camming surface on the proximal end of the one body engages a bevel surface on the pin to move the pin to the second position when the body members are brought together.

Alternatively the latching means comprises a slot in the proximal end of one body member and a pin coupled to the other body member. A latch member is pivotally coupled to the one body member spaced apart from the slot and rotatable between a latching position and a second position. A cam surface on the latch member moves the latch member to the second position when the pin enters the slot. The latch member is biased to return to the latching position about the pin as the pin moves farther into the slot.

BRIEF DESCRIPTION OF THE DRAWINGS

FIG. 1 is a side elevational view of the instrument of the present invention in the staple inserting and clinching position.

FIG. 2 is a top plan view of the instrument shown in FIG. 1.

FIG. 3 is a sectional view taken along the lines and arrows 3—3 of FIG. 1.

FIG. 4 is a sectional view taken along the lines and arrows 4—4 of FIG. 1.

FIG. 5 is a side elevational view of a first body member and its staple inserting jaw;

FIG. 6 is a side elevational view of the pusher bar together with its wedge and knife;

FIG. 7 is a side elevational view of a second body member together with its staple clinching jaw and the instrument latching means carried thereby.

DETAILED DESCRIPTION OF THE DRAWINGS

Figure 9:
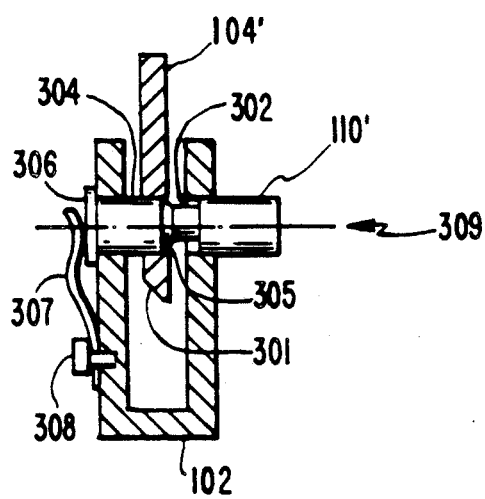
FIG. 9 is a proximal end view in cross section of the first and second body members coupled together taken through the slot of the second body member as shown in FIG. 8 and showing an alternate embodiment pin portion of the first body member.

Referring to the drawings, a surgical instrument for internal stapling of gastric and intestinal walls with spaced parallel rows of metallic staples is shown designated generally 100. The instrument 100 includes first and second body members 102 and 104 having a elongated staple inserting jaw 106 and a staple clinching jaw 108, respectively. The second body member 104 is detachably and pivotally connected to the first body member 102 adjacent their proximal ends by means of a pivot pin 110 on the body member 102 received in a slot 112 on the body member 104. Means designated generally 114 to be described in more detail hereinafter are provided to releasably lock the body members 102 and 104 together with the jaws 106 and 108 carried thereby in operational position.

Referring to FIG. 3, a longitudinal groove 120 is provided in an inner surface 121 of the staple inserting jaw 106 which groove opens towards the staple clinching jaw 108. The staple clinching jaw 108 also has a longitudinal slot 122 in its inner surface 123 and in alignment with the groove 120. The staple inserting jaw 106 includes a plurality of longitudinally spaced staple receiving recesses 224 and 226 in the sidewall 228 and 230, respectively, of the groove 120 and slidably disposed in the recesses 224 and 226 are staple driving members 224' and 226'. The staple driving members 224' and 226' are provided with lugs 232 and 234, respectively, projecting into the groove 120. A staple cartridge removable from the jaw 106 and including the longitudinal groove, staple recesses, staples, staple driving members, etc. could be provided. The cartridge would be loadable into an appropriate recess in the staple inserting jaw 106. Many examples of such cartridges are provided in the prior art, e.g. see U.S. Pat. No. 3,490,675.

Referring now to FIGS. 1 and 6, an elongated pusher bar 140 is shown which acts as a staple driver actuating means. The pusher bar 140 includes a laterally projecting pin 142 slidably received in a slot or groove 144 in the body member 102. The bar 140 is also slidably received in the groove 120 of the staple inserting jaw 106. The pusher bar 140 includes at its distal end a wedge 146 and, proximally thereof, a downwardly projecting knife blade 148. The bar 140 is provided adjacent the proximal ends thereof with a finger or thumb engaging tab 150 to be used to operate bar 140. In order to prevent inadvertent operation of the bar 140 a spring 152 is provided attached to the body member 102 at 154 and with a pin 156 projecting into a notch 158 on the bar 140.

Referring to FIG. 4, the staple clinching jaw 108 is provided with staple clinching anvil portion 160 disposed opposite the staple receiving recesses 224 and 226 in the staple inserting jaw.

The general construction and operation of the illustrated instrument is similar to many of the instruments described in several patents, most notably U.S. Pat. No. 3,079,606. Accordingly, the following description will only deal in detail with modified features of the instrument and for a fuller understanding of the principles and operation of the instrument, reference may be made to the above patent the disclosure of which is incorporated herein by reference.

Referring now to FIG. 1 and FIGS. 5-7, the improved locking means 114 comprises a toggle joint having one end 162 pivotally attached to the second body member 104 at 164 and a second end 166 adapted to engage the outer surface 168 of the second body member on the second body member's opposite side from the inner surface 123. The toggle joint further comprises a knee portion 170 intermediate the ends 162 and 166.

The toggle joint includes a lever bar 174 with one end forming the end 166 of the toggle joint and with an opposite free end 176, and a linking bar 178 with one end forming the end 162 of the toggle joint and the opposite end 180 pivotally connected to the lever bar 174 intermediate its ends 166 and 176.

End 166 of toggle joint 114 includes a roller 182 adapted to engage and roll along outer surface 168 when the knee 170 of the joint is straightened by pushing it toward the second body member 104. End 166 also includes a pin 184 coupled to spaced apart ear portions 186 at end 166 of lever bar 174. The ear portions extend laterally away from the lever bar 174 at end 166. The toggle joint 114 further includes a handle portion 169 connected in any suitable manner to the lever bar 174.

The first body member includes a frame 188 having a handle portion 190 and spaced apart sides 192 which extend away from the first body member 102 on opposite sides of the proximal portion of the jaw 106. The sides 192 are adapted to receive the second body member 104 therebetween. This helps to insure that the jaws 106 and 108 are in proper lateral alignment during operation of the instrument. A further aligning and locating means is provided in the form of a pointed pin 193 secured to the staple clinching jaw 108 adjacent the outer end thereof and the pointed end of the pin is received in the groove 120 in the staple inserting jaw 106 when the parts are in the operative position.

The spaced apart sides 192 each have a slot 196 aligned with on another for receiving the pin 184 on the end 166 of lever bar 174. The slot has a wide open mouth 197 which narrows at its distal end as it extends generally longitudinally from the proximal end of the instrument to the distal end. The slots are located in a portion of the spaced apart sides 192 which extend beyond the second body member 104 when the body members are in the tissue gripping position.

With the tissue to be sutured placed between the jaws and with the first and second body members coupled together by placing the pin 110 in groove 112, the instrument is locked together as follows: the knee 170 of the toggle joint 114 is moved toward the second body member 104 by squeezing the handle portions 169 and 190 together. As the end 166 rolls along surface 168 the pin 184 will engage the mouth 197 of the slots 196. As the knee is straightened further the longitudinal action of the end 166 along the surface 168 is translated into a clamping force by pin 184 on slot surface 198 pulling the jaws 100 and 108 together about the tissue.

Figure 8:
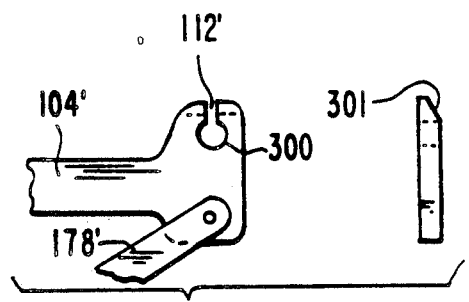
FIG. 8 is a side elevational view of an alternate embodiment of a proximal portion of the second body member of FIG. 7.

Referring now to FIGS. 8 and 9 a means for quick latching of the proximal ends of the body members 102' and 104' is provided FIG. 8 shows a modification 112' to the slot 112. Slot 112' is shaped like a key hole with the narrow part of the slot 112' extending to the side edge of enlarged proximal end of body member 104'. The narrow part of the slot is in communication with an interior circular hole portion 300. The side edge of the enlarged proximal end containing the slot has a cam surface 301.

In FIG. 9, a modified pin 110' is coupled to the parallel and spaced apart walls of the proximal end of the first body member by a rivet or fastener 308. A spring 307 attached to the body member 104 at 308 holds the pin 110' in place and biases it to a first position. A portion of the pin 110' protrudes through a hole in the wall of body member 104' opposite the fastener 308.

In general, the diameter of the pin 110' is larger than the narrow part of slot 112' but the pin 110' has a narrow central portion 302 with an adjacent bevel surface 305 which transitions between the central narrow portion and the remainder of the pin. When the cam surface 301 of body member 104' engages the bevelled surface 305, the pin 110' moves against the spring 307 aligning the narrow portion 302 of the pin 110' with the narrow part of the key hole slot 112'. As the pin moves, into the circular portion 300 of the slot 112', the spring 307 moves the pin into its biased first position with the larger diameter of the pin within the hole 300 and aligned with the narrow part of the slot. This captures the pin 110' within the slot 112' since the larger diameter of the pin is larger than the narrow part of the slot. The body members are thereby latched together. By latching, it is meant that the parts are fastened together. The latch is easily released by simply pushing pin 110' axially against the spring 307 in the direction of arrow 309 until slot 112' can slip over the narrow portion 302 of the pin 110'.

Figure 10:
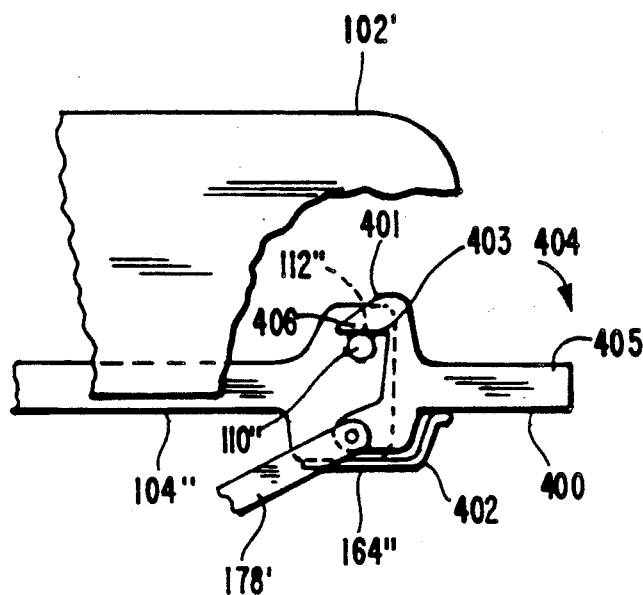
FIG. 10 is a second alternate embodiment of the proximal portions of the first and second body members shown in elevation and partially broken away.

An alternate latch mechanism for operating with the structure of FIG. 8 is shown in FIG. 10. A latch member 400 is attached by pin 164" to the body member 104" spaced apart from slot 112". Latch member 400 is free to rotate about pin 164 from the latch position shown in FIG. 10 to a second position The latch member is biased in the latch position by spring 402 which is mounted to body member 104" and engages a handle portion 405 which extends away from the proximal position of the instrument.

As the pin 110" is inserted into the slot 112", the cam surface 401 engages the pin rotating the latch member 400 in the direction of arrow 404. As the body member 104" is pushed farther in the direction of body member 102", the latch member 400 rotates farther until the latch member slips by pin 110" and the interior flat surface 403 on the hook portion 406 engages the pin 110" to latch the body members together. To detach the body members, the member 405 is pushed in the direction 404 releasing pin 110" from slot 112".

It will be obvious to those skilled in the art that various changes may be made in the invention without departing from the spirit and scope thereof and therefore the invention is not limited by that which is shown in the drawings and described in the specification, but only as indicated in the appended claims.

What is claimed is:

1. A surgical stapling instrument comprising:
    first and second body members pivotally and detachably connected to each other, each having an elongated jaw, one of said jaws being adapted to receive at least two spaced apart longitudinal rows of staples;
    an elongated bar slidable longitudinally relative to said jaws for ejecting staples from an inner face of said jaws and shaping the staples against anvil means provided on an opposing inner face of the other of said jaws to form a pair of spaced staple rows in tissue gripped between said jaws;
    means for releasably locking said jaws in a tissue gripping staple inserting position, said locking means comprising:
    a toggle joint having a first end pivotally mounted to said second body member;
    a second end adapted to engage said second body member distally of said first end of said toggle joint, said toggle joint including a knee portion disposed between said first and second ends, said second end also adapted to engage a portion of said first body member to lock said first and second jaws in the tissue gripping position when said knee is straightened.

2. The instrument of claim 1 wherein said toggle joint comprises a lever bar which engages said second body member at one end and a linking bar which is pivotally mounted to said second body member at one end and is pivotally connected to said lever bar intermediate its ends.

3. The instrument of claim 2 wherein said lever bar comprises a roller mounted to said one end and freely rotatable about its axis for low friction engagement with an outer side of said second body member opposite the inner side of said second body member containing said inner face.

4. The instrument of claim 2 wherein said frame of said first body member has a handle portion and said instrument comprises a handle portion attached to said lever bar wherein said jaws can be readily locked together.

5. The instrument of claim 1 wherein said first body member comprises a frame having a portion with spaced apart sides which extend away from said first body member and are adapted to receive said second body member therebetween, said spaced apart sides each having a slot aligned with one another, said slots adapted to receive a pin mounted on said one end of said lever bar.

6. The instrument of claim 1 wherein one of said body members comprises a slot at its proximal end and the other of said body members comprises a pin for pivotal engagement with said slot.

7. The instrument of claim 1 wherein said toggle joint second end engages said second body member at the proximal end of said second body member jaw.

8. The instrument of claim 1 wherein said instrument further comprises latching means for releasably latching said first and second body members at their proximal ends.

9. The instrument of claim 8 wherein said latching means comprises:
    a key hole slot in the proximal end of one of said body members; and
    a pin coupled to the other of said body memebers and movable between a first and second position and biased in said first position, said pin having a narrowed diameter region for passing through the narrow portion of said key hole slot when said pin is in said second position.

10. The instrument of claim 9 wherein the proximal end of said one body member adjacent said key hole slot comprises a cam surface and portion of the surface of said pin adjacent said narrowed diameter surface is bevelled so that when said cam and bevelled surfaces engage said pin moves from said biased first position to said second position.

11. The instrument of claim 8 wherein said latching means comprises:
    a slot in the proximal end of one of said body members;
    a pin coupled to other of said body members and adapted to fit within said slot; and
    a latch member pivotally coupled to said one body member and spaced apart from said slot, said latch member rotatable from a latching position to a second position and biased in said latching position, said latch member comprising a cam surface which engages said pin when said pin enters said slot to move said latch member to said second position until said pin moves farther into said slot whereupon said latch member returns to said latching position about said pin.

12. A surgical instrument comprising:

first and second body members pivotally and detachably connected to each other, each having an elongated jaw, one of said jaws being adapted to receive at least two spaced apart longitudinal rows of staples;

an elongated bar slidable longitudinally relative to said jaws for ejecting staples from an inner face of said jaws and shaping the staples against anvil means provided on an opposing inner face of the other of said jaws to form a pair of spaced staple rows in tissue gripped between said jaws;

means for releasably locking said jaws in a tissue-gripping staple inserting position; and latching means for releasably latching said first and second body members at their proximal ends, said latching means comprising:

a key hole slot in the proximal end of one of said body members; and a pin coupled to the other of said body members and movable between a first and second position and biased in said first position, said pin having a narrowed diameter region for passing through the narrow portion of said key hole slot when said pin is in said second position.

13. The instrument of claim 12 wherein the proximal end of said one body member adjacent said key hole slot comprises a cam surface and portion of the surface of said pin adjacent said narrowed diameter surface is bevelled so that when said cam and bevelled surfaces engage said pin moves from said biased first position to said second position.

14. A surgical instrument comprising:

first and second body members pivotally and detachably connected to each other, each having an elongated jaw, one of said jaws being adapted to receive at least two spaced apart longitudinal rows of staples;

an elongated bar slidable longitudinally relative to said jaws for ejecting staples from an inner face of said jaws and shaping the staples against anvil means provided on an opposing inner face of the other of said jaws to form a pair of spaced staple rows in tissue gripped between said jaws;

means for releasably locking said jaws in a tissue-gripping staple inserting position; and latching means for releasably latching said first and second body members at their proximal ends, said latching means comprising:

a slot in the proximal end of one of said body members;

a pin coupled to other of said body members and adapted to fit within said slot; and a latch member pivotally coupled to said one body member and spaced apart from said slot, said latch member rotatable from a latching position to a second position and biased in said latching position, said latch member comprising a cam surface which engages said pin when said pin enters said slot to move said latch member to said second position until said pin moves farther into said slot whereupon said latch member returns to said latching position about said pin.

15. A surgical stapling instrument comprising:

first and second body members pivotally and detachably connected to each other, each having an elongated jaw, one of said jaws being adapted to receive at least two spaced apart longitudinal rows of staples;

an elongated bar slidable longitudinally relative to said jaws for ejecting staples from an inner face of said jaws and shaping the staples against anvil means provided on an opposing inner face of the other of said jaws to form a pair of spaced staple rows in tissue gripped between said jaws;

means for releasably locking said jaws in a tissue gripping staple inserting position, said locking means comprising:

a toggle joint comprising a linking bar having a first end pivotally mounted to said second body member;

a lever bar, one end of which is adapted to engage said second body member distally of said first end of said linking bar, said lever bar being pivotally connected intermediate its ends to the other end of said linking bar, said one end of said lever bar also adapted to engage a portion of said first body member to lock said first and second jaws in the tissue gripping position when said lever bar is straightened relative to said linking bar.

* * * * *